US011344291B2

(12) United States Patent
Sauer

(10) Patent No.: US 11,344,291 B2
(45) Date of Patent: May 31, 2022

(54) MINIMALLY INVASIVE SUTURE PLACEMENT SYSTEM AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 258 days.

(21) Appl. No.: 16/367,781

(22) Filed: Mar. 28, 2019

(65) Prior Publication Data

US 2019/0298336 A1  Oct. 3, 2019

Related U.S. Application Data

(60) Provisional application No. 62/649,528, filed on Mar. 28, 2018.

(51) Int. Cl.
| | | |
|---|---|---|
| *A61B 17/04* | (2006.01) | |
| *A61B 90/00* | (2016.01) | |
| *A61B 17/06* | (2006.01) | |
| *A61B 17/00* | (2006.01) | |

(52) U.S. Cl.
CPC ...... *A61B 17/0469* (2013.01); *A61B 17/0482* (2013.01); *A61B 17/0487* (2013.01); *A61B 17/0057* (2013.01); *A61B 17/0491* (2013.01); *A61B 17/06066* (2013.01); *A61B 2090/0811* (2016.02)

(58) Field of Classification Search
CPC ............ A61B 17/0469; A61B 17/0482; A61B 17/0487; A61B 17/0491
See application file for complete search history.

(56) References Cited

U.S. PATENT DOCUMENTS

| | | | |
|---|---|---|---|
| 6,629,984 B1* | 10/2003 | Chan ................. | A61B 17/0482 606/139 |
| 2003/0216755 A1* | 11/2003 | Shikhman ............. | A61B 17/11 606/144 |
| 2006/0052802 A1 | 3/2006 | Sterman et al. | |

(Continued)

FOREIGN PATENT DOCUMENTS

| | | |
|---|---|---|
| EP | 2005892 | 2/2007 |
| EP | 1862125 | 5/2007 |
| WO | WO932640 | 2/1993 |

OTHER PUBLICATIONS

Office Action from Related Application, dated Mar. 15, 2021, Adam, Mohammed Sohail.

(Continued)

*Primary Examiner* — Kelly J Bekker
*Assistant Examiner* — Mohammed S Adam
(74) *Attorney, Agent, or Firm* — Michael E. Coyne; Christopher B. Miller

(57) ABSTRACT

A suture placement system is disclosed. The suture placement system has a plate defining a first opening spaced from a second opening. The suture placement system also has a first lumen having proximal and distal ends, wherein the distal end of the first lumen is coupled to the first opening. The suture placement system further has a second lumen having proximal and distal ends, wherein the distal end of the second lumen is coupled to the second opening. The suture placement system also has a guide coupled to the plate. A method of minimally invasive suture placement is also disclosed.

24 Claims, 4 Drawing Sheets

(56) References Cited

U.S. PATENT DOCUMENTS

| | | | |
|---|---|---|---|
| 2006/0069398 A1* | 3/2006 | Suzuki | A61B 17/0482 606/148 |
| 2008/0154286 A1* | 6/2008 | Abbott | A61B 17/0487 606/139 |
| 2009/0062817 A1* | 3/2009 | Suzuki | A61B 17/3403 606/144 |
| 2009/0264905 A1* | 10/2009 | Funada | A61B 17/04 606/146 |
| 2009/0292302 A1 | 11/2009 | Manzo | |
| 2011/0301619 A1* | 12/2011 | Walters | A61B 17/0057 606/144 |
| 2015/0216514 A1 | 8/2015 | Weisbrod et al. | |
| 2018/0235602 A1 | 8/2018 | Dang et al. | |

OTHER PUBLICATIONS

Journal Entry; Jun. 11, 2004; Suematsu et al., Yoshihiro; Journal Entry Three-Deminsional echocardiography guided beating-heart surgery without cardiopulmonary bypass: A feasibility study, pp. 1-9.

Foreign Search Report; dated Jul. 22, 2020; Biegler, Marcel; Foreign Search Report from EP20166790, pp. 1-7.

Foreign Search Report; dated Jul. 29, 2020; Geiss, Oana; Foreign Search Report from EP20166182, pp. 1-8.

* cited by examiner

MINIMALLY INVASIVE SUTURE PLACEMENT SYSTEM AND METHODS THEREOF

RELATED APPLICATIONS

This application claims priority to U.S. Provisional Patent Application No. 62/649,528 filed Mar. 28, 2018 and entitled, "MINIMALLY INVASIVE SUTURE PLACEMENT SYSTEM AND METHODS THEREOF". The 62/649,528 application is also hereby incorporated by reference in its entirety.

FIELD

The claimed invention relates to surgical devices, and more specifically to suture placement systems for use in minimally invasive surgeries.

BACKGROUND

Modern advances in cardiac surgery have made it possible to repair or replace heart valves using minimally invasive surgical techniques. As minimally invasive techniques have improved, surgeons have been able to operate on patients through smaller and smaller access holes, resulting in less perioperative pain and shorter recovery times. A main focus of innovation in minimally invasive cardiac surgery has been on automated suturing technology for placement of suture stitches through tissue and also through the sewing cuffs of prosthetic devices such as, for example, annuloplasty rings. For example the RAM® Device, sold by LSI Solutions, Inc. of Victor, N.Y. (www.lsisolutions.com), is particularly effective for the automatic placement of pledgeted sutures in tissue, such as an aortic annulus during minimally invasive aortic valve surgery. The RAM® Device may be used in conjunction with a SEW-EASY® Device, also sold by LSI Solutions, Inc., for the automated placement of those same sutures through a sewing cuff of a prosthetic heart valve or an annuloplasty ring. By utilizing such automated suturing tools, surgeons are able to accomplish most of their surgical actions through very small incisions (on the order of 5 cm) made in one of the intercostal spaces between a patient's ribs. This is particularly beneficial to the patient, as the previous alternatives were much larger openings, including the use of a full sternotomy. Minimally invasive surgery is less traumatic to patients and often enables them to be on cardio-pulmonary bypass (CPB) machines for shorter times, thereby improving patient outcomes and reducing recovery times.

While more steps continue to be taken to reduce the amount of time a patient must be on CPB, surgeons continue to push the boundaries of what is possible by striving to be able to perform certain surgeries on a beating heart without the need for CPB. It would be even more desirable to be able to perform specific cardiac surgical procedures on a beating heart under minimally invasive conditions. For example, it would be highly desirable to be able to perform a tricuspid valve repair through a cannula placed between a patient's ribs and into the right atrium of the heart while the heart is still beating. The pressure in the right atrium is such that the blood would tend to fill partially into such a cannula, and of course, there would be blood within the right atrium which would also, unfortunately, completely obscure a surgeon's view of the right atrium and the tissues of the tricuspid valve if such an approach were to be taken. Even echocardiography, on its own, would have a difficult time allowing the surgeon to orient a suturing device through the blood field for a series of related stitches. Therefore, it would be desirable to have a minimally invasive suture placement system and method which would enable reliable suture placement around a cardiac valve, such as a tricuspid valve, even under conditions of zero direct and zero endoscopic visibility to enable minimally invasive beating heart surgery for better patient outcomes.

SUMMARY

A suture placement system is disclosed. The suture placement system has a plate defining a first opening spaced from a second opening. The suture placement system also has a first lumen having proximal and distal ends, wherein the distal end of the first lumen is coupled to the first opening. The suture placement system further has a second lumen having proximal and distal ends, wherein the distal end of the second lumen is coupled to the second opening. The suture placement system also has a guide coupled to the plate.

A method of minimally invasive suture placement is also disclosed. A minimally invasive suturing device is used to place a stitch of a first implant suture in tissue. A first end of the implant suture is pulled through a second lumen coupled to a plate. The first end of the implant suture is secured relative to the second lumen such that a distal end of the second lumen is held against the tissue. A second end of the implant suture is secured relative to a first lumen such that a distal end of the first lumen is held against the tissue. A follower on the minimally invasive suturing device is slid down a guide coupled to the plate at a fixed spacing from at least one of the first and second lumens until a tissue bite area of the suturing device coupled to the follower contacts the tissue. A stitch of a second implant suture is placed into the tissue at a position determined at least in part by an arc which the minimally invasive suturing device is able to follow by having the follower pivot on the guide.

BRIEF DESCRIPTION OF THE DRAWINGS

The claimed invention relates to surgical devices, and more specifically to suture placement systems for use in minimally invasive surgeries.

Figure 1:
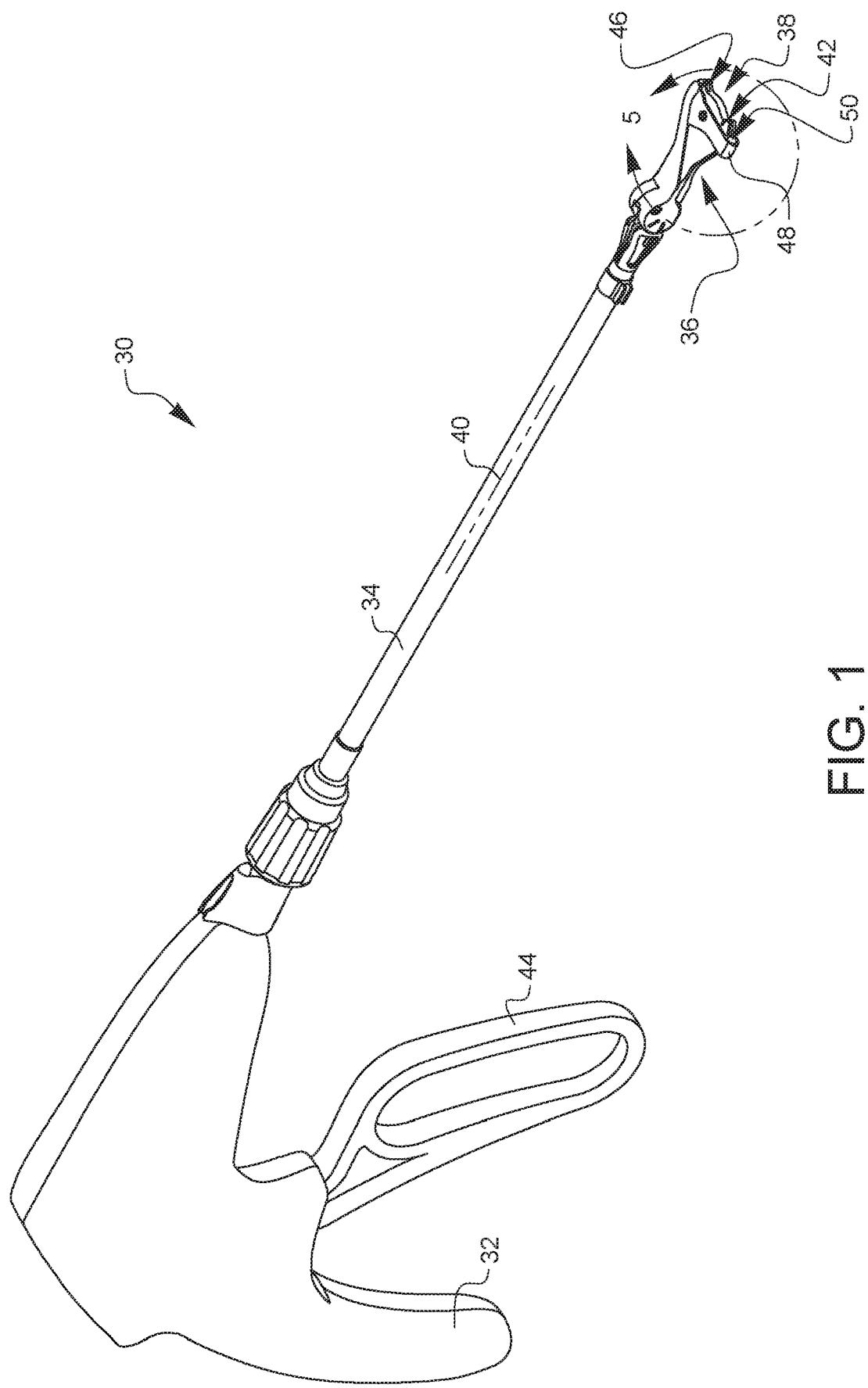
FIG. 1 illustrates one embodiment of a minimally invasive suturing device 30.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 illustrates one embodiment of a minimally invasive suturing device 30. The suturing device 30 has a handle 32 from which a shaft 34 extends. A distal sewing tip 36 resides at the end of the shaft 34. This particular suturing device 30 has an arcuate tissue bite area 38 facing distally along the longitudinal axis 40 of the suturing device 30. Although not shown in this view, an implant suture (for tissue implantation) with a ferrule on at least a first end of the implant suture may be loaded into the device 30 such that the ferrule on the end of the suture (not shown in this view) is held by a ferrule holder 42 in the device tip 36. In operation, a surgeon uses the handle 32 to manipulate the tissue bite area 38 against tissue where a suture stitch is desired. A lever 44 is then squeezed to actuate a needle (not visible in this view) to exit an opening 46 in the device tip 36, traverse through the tissue in the tissue bite area 38, and move into contact with the ferrule stored in the ferrule holder 42. The contact of the needle with the ferrule causes the ferrule to become attached to the needle, and when the surgeon releases the handle 44, the needle (with its attached ferrule) retracts back through the tissue in the tissue bite area 38 while also pulling the attached implant suture through the tissue. Thus, a suture stitch is formed in the tissue. This manner of using a needle with a ferrule for suturing is known to those skilled in the art, and a variety of needle configurations, including, but not limited to single needle devices, multiple needle devices, curved needle devices, and straight needle devices are compatible with the claimed invention. For simplicity, only a single suturing device 30 is discussed as an example.

A novel feature on the device tip 36 of this embodiment is a follower 48 coupled to the minimally invasive suturing device 30. The follower 48 defines an opening 50 which is configured for slideable engagement with a guide (not visible in this view, but the guide is discussed in more detail with regard to FIG. 2).

Figure 2:
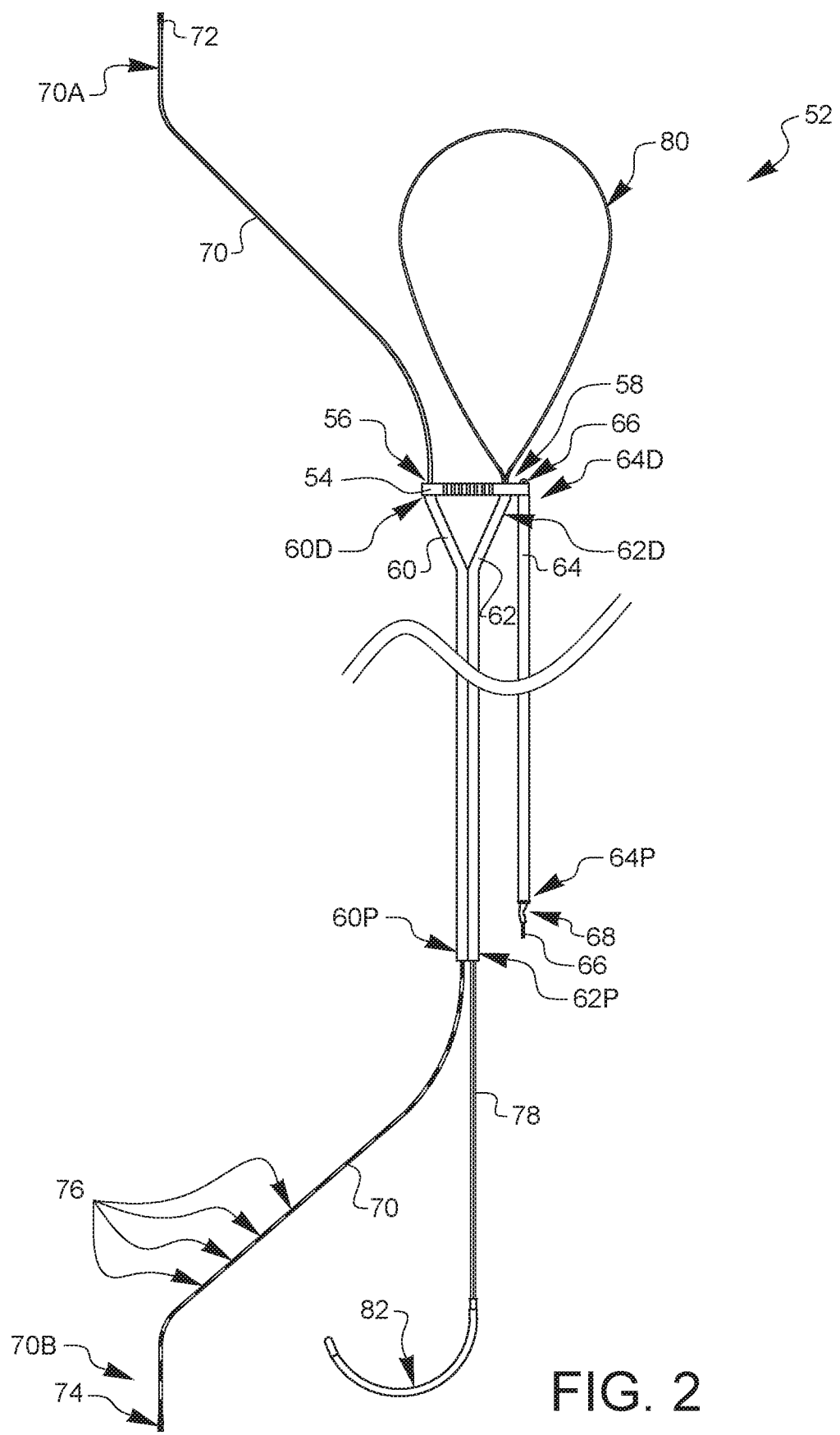
FIG. 2 illustrates one embodiment of a suture placement system.

FIG. 2 illustrates one embodiment of a suture placement system 52. The suture placement system 52 has a plate 54 defining a first opening 56 which is spaced from a second opening 58. The suture placement system 52 has a first lumen 60 having a proximal end 60P and a distal end 60D. The distal end 60D of the first lumen 60 is coupled to the first opening 56 in the plate 54. The suture placement system 52 also has a second lumen 62 having a proximal end 62P and a distal end 62D. The distal end 62D of the second lumen 62 is coupled to the second opening 58 in the plate 54. A guide 64 is also coupled to the plate 54.

In this embodiment, the second opening 58 is located between the first opening 56 and the point where the guide 64 is coupled to the plate 54. Also in this embodiment, the guide 64 is a tube which is removably coupled to the plate 54 by an attachment suture 66 that engages the plate 54, passes through the distal end 64D of the guide tube 64, and is secured near a proximal end 64P of the guide tube 64 by a fastener 68 to keep the guide tube 64 coupled to the plate 54. One non-limiting example of a suitable fastener 68 is a crimpable titanium knot, such as the Ti-KNOT® fastener from LSI Solutions, Inc of Victor, N.Y. (www.lsisolutions.com). If it is ever desired to remove the guide 64 from the plate 54, the fastener 68 just has to be cut from the attachment suture 66 and the tube will release. In other embodiments, the guide 64 could be coupled to the plate 54 using other techniques, including, but not limited to gluing, ultrasonic welding, or simply fabricating both parts from a single continuous piece of material. The guide 64 may have a variety of cross-sectional shapes, including, but not limited to circular, oval, square, rectangular, triangular, notched, and keyed.

The follower 48 described in FIG. 1 is configured for slideable engagement with the guide 64 of FIG. 2. As such, the opening 50 defined by the follower 48 should have a shape which is compatible for slideable engagement with the guide 64. In embodiments where the guide 64 comprises a fastener 68, the opening 50 of the follower 48 should be sized to fit over the fastener 68 before going onto the guide 64. In other embodiments, the opening 50 may comprise a partially closed opening which can be set against the guide 64 without needing to pass over the fastener 68.

In the embodiment of FIG. 2, a portion of the first and second lumens 60, 62 are bonded together. As will be noted later in this discussion, respective ends of an implantation suture will be exiting the proximal ends 60P, 62P of the lumens 60, 62. By having the first and second lumens 60, 62 bonded together, especially at the proximal ends 60P, 62P, a single clamp may be used to grip the lumens 60, 62 to hold the suture ends in place. In other embodiments, the first and second lumens 60, 62 may not be bonded together at all, but could be separate. In still other embodiments, at least a portion of the first and second lumens may be housed within the same suture tube.

The suture placement system 52 also has an implant suture 70 having a first ferrule 72 on a first end 70A of the implant suture 70. The implant suture 70 also has a second ferrule 74 on a second end 70B of the implant suture 70. The implant suture 70 is partially located within the first lumen 60 such that the first end 70A of the implant suture 70 with the first ferrule 72 extends from the distal end 60D of the first lumen 60. The second end 70B of the implant suture 70 with the second ferrule 74 extends from the proximal end 60P of the first lumen 60. In this embodiment, the implant suture 70 has one or more markings 76 to differentiate the second end 70B from the first end 70A of the implant suture 70.

The suture placement system 52 also has a snare 78 having a snare loop 80 and a snare handle 82. The snare 78 is at least partially located within the second lumen 62 such that at least a portion of the snare loop 80 extends from the distal end 62D of the second lumen 62, while at least a portion of the snare handle 82 extends from the proximal end 62P of the second lumen 62. Depending on the embodiment, the snare handle 82 does not have to be a separate piece from the wire, suture, or other material which forms the snare loop 80. The snare handle 82 could simply be the ends of the material which forms the snare loop 80.

Figure 3:
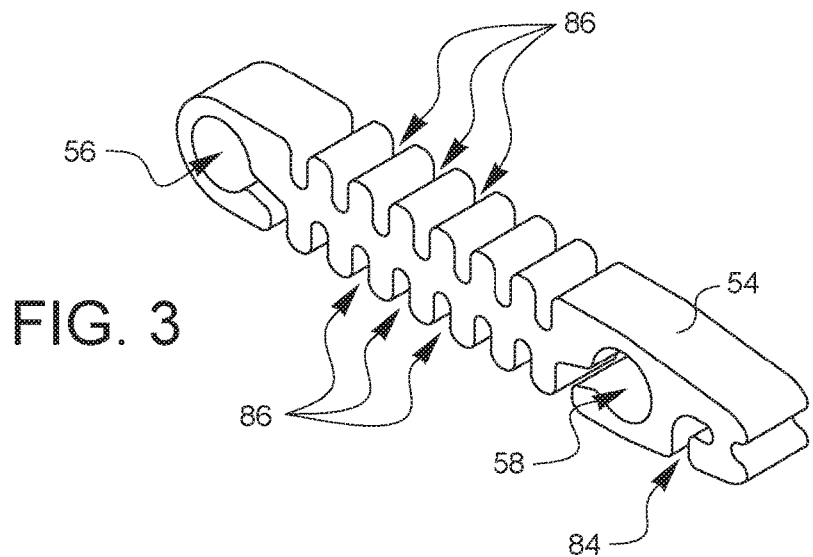
FIG. 3 is a proximal-top-right perspective view of one embodiment of a plate which is part of the suture placement system of FIG. 2.
Figure 4E:
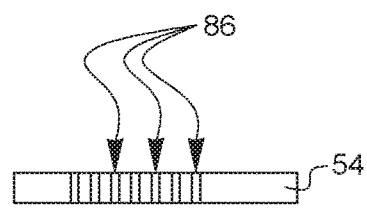
FIGS. 4A, 4B, 4C, 4D, 4E, and 4F are proximal, left, right, distal, top, and bottom elevational views, respectively, of the plate 54 from FIG. 3.
Figure 4B:
Figures 4A, 4C:
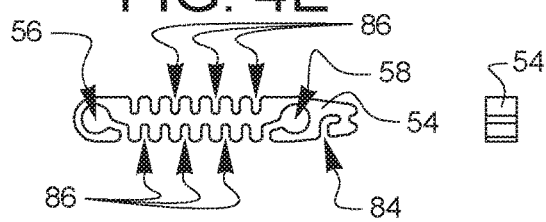
Figure 4D:
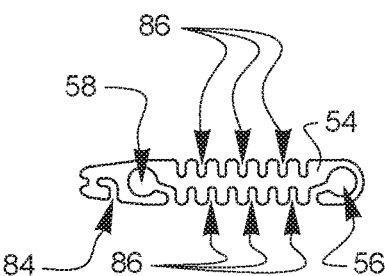
Figure 4F:
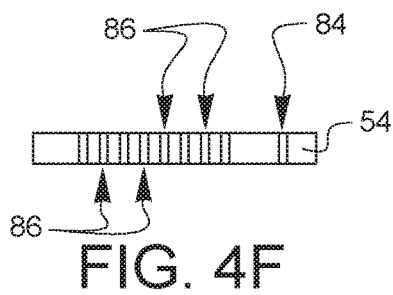

FIG. 3 is a proximal-top-right perspective view of one embodiment of the plate 54 discussed above as part of the suture placement system. The first and second openings 56, 58, where the first and second lumens (not shown in this view), respectively, are coupled to the plate, are visible in this view. An attachment feature 84 for the guide 64 (not shown in this view) is also defined by the plate 54. The attachment suture 66 may be threaded around this attachment feature 84 and held in place as described above. In this embodiment, the plate 54 has surface variations 86 which are configured to make the plate visible on an echocardiogram. In this example, the surface variations 86 take the form of notches, but other embodiments could have other shapes for surface variations, including no surface variations at all. The suture placement system is intended to be used in a beating heart where blood will likely obscure the distal portions of the system (including the plate) from being seen with the naked eye, loops, or an endoscope. It will be advantageous to be able to see the system on an echocardiogram, so if surface variations are not used, it may be desirable in some embodiments to coat at least a portion of the plate with a coating configured to make the plate visible on an echocardiogram. Such coatings are known to those skilled in the art. Such coatings could also be used in combination with surface variations 86. Furthermore, one or more of the plate 54, the first lumen 60, the second lumen 62, and the guide 64 may have a coating configured to make these parts visible on an echocardiogram. Additionally, it may be desirable to add such coatings to the follower 48 on the suturing device 30 and/or the distal tip 36 of the suturing device 30.

FIGS. 4A, 4B, 4C, 4D, 4E, and 4F are proximal, left, right, distal, top, and bottom elevational views, respectively, of the plate 54 from FIG. 3.

In practice, the first ferrule 72 on the first end 70A of the implant suture 70 is loaded into the ferrule holder 42 of the minimally invasive suturing device 30. The remainder of the suture placement system 52 may be held nearby the suturing device 30 while the tissue bite area 38 is positioned against a desired tissue. For an example, we will say the tissue bite area 38 is positioned against a portion of the annulus of a tricuspid valve during a minimally invasive beating heart surgery. Using echocardiography a surgeon should be able to position the tissue bite area 38 appropriately on the annulus, especially if some feature on the distal tip 36 is configured to make it echo-visible. The difficulty comes in trying to place subsequent stitches in appropriate relation to the first stitch of the implant suture. The claimed invention, and its equivalents, provide a novel solution for this difficulty.

After the first implant suture 70 is stitched through the annulus, the suturing device 30 is removed from the blood field and the first ferrule 72 is released from the suturing device. The first end 70A of the implant suture 70 is pulled through the second lumen 62 by placing the first end 70A in the snare loop 80 and pulling it proximally through the second lumen 62 with the handle 82. The distal end 62D of the second lumen 62 and/or the second opening 58 in the plate 54 can be positioned against the tissue and the first end 70A of the implant suture 70 may be secured relative to the second lumen 62, for example, by placing a mosquito or other suitable clamp on the proximal end 62P of the second lumen 62. As configured in the embodiment of FIG. 2, the second end 70B of the implant suture 70 is already passed through the first lumen 60. If this was not the case, an embodiment could be provided with a separate snare for pulling the second end 70B of the implant suture 70 through the first lumen 60. In our example, however, the second end 70B is already through the first lumen 60. The second end 70B of the implant suture 70 may then be secured relative to the first lumen 60 such that the distal end 60D of the first lumen 60 and/or the first opening 56 in the plate 54 can be positioned against the tissue and the second end 70B of the implant suture 70 may be secured relative to the first lumen 60, for example, by placing a mosquito or other suitable clamp on the proximal end 60P of the first lumen 60. Alternatively, a single clamp may be used on the proximal ends 60P, 62P of the first and second lumens 60, 62 after the suture placement system is positioned against the tissue. In other embodiments, one or more integrated suture locks may come coupled to the proximal ends 60P, 62P of the first and/or second lumens 60, 62.

Figure 5:
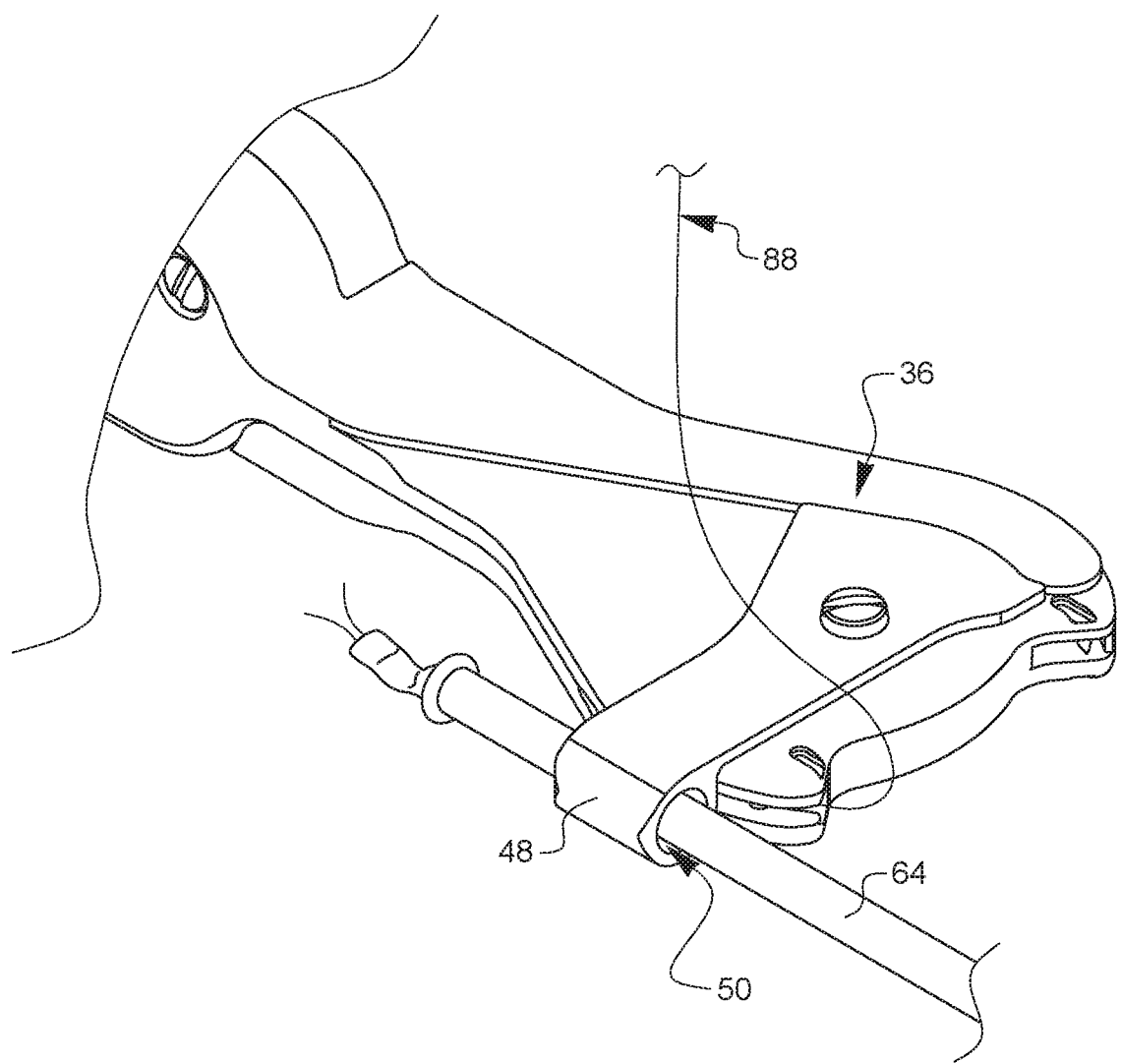
FIG. 5 is an enlarged view of the distal tip of the suturing device of FIG. 1 wherein a follower has been placed over a guide of the suture placement system of FIG. 2.

With the suture placement system 30 held in place against the tissue, a second implant suture 88 is then loaded into the distal tip 36 of the suturing device, and the opening 50 of the follower 48 is placed over the guide 64 (as shown in FIG. 5) of the suture placement system 52 which is being held in position against the tissue (not shown in this view). The follower 48 on the minimally invasive suturing device may then be slid down the guide 64 coupled to the plate 54 until the tissue bite area 38 of the suturing device coupled to the follower 48 contacts the tissue. Since the guide 64 is coupled to the plate 54 at a fixed spacing from at least one of the first and second lumens 60, 62, and since the suturing device is now pivotable via the follower 48 on the guide 64, the suturing device may then be used to place a stitch of the second implant suture 88 into the tissue at a position determined at least in part by an arc which the minimally invasive suturing device is able to follow by having the follower 48 pivot on the guide 64. An echocardiogram can help determine the best position for the stitch of the second implant suture relative to the annulus, and the surgeon has the confidence of a reliable spacing relative to the previous implant suture thanks to the novel suture placement system and follower disclosed herein. Although not illustrated herein, the second implant suture 88 may be part of another suture placement system so that the process may be repeated as desired until a series of stitches have been placed around the tricuspid annulus. This system and method enables reliable, repeatably spaced stitches to be placed in a blood field where direct or endoscopic visualization is not possible.

Various advantages of a minimally invasive suture placement system and methods thereof have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A suture placement system, comprising:
   a plate defining a first opening spaced from a second opening;
   a first lumen having proximal and distal ends and an intermediate point between the proximal end and the distal end, wherein the first lumen has a first segment extending from the proximal end to the intermediate point and a second segment extending from the intermediate point to the distal end, wherein the first segment of the first lumen extends along a first segment axis and the second segment of the first lumen extends along an axis that forms an obtuse angle with the first segment axis of the first lumen, and wherein the distal end of the first lumen is coupled to the first opening;
   a second lumen having proximal and distal ends and an intermediate point between the proximal end and the distal end, wherein the second lumen has a first segment extending from the proximal end to the intermediate point and a second segment extending from the intermediate point to the distal end, wherein the first segment of the second lumen extends along a first segment axis and the second segment of the second lumen extends along an axis that forms an obtuse angle with the first segment axis of the second lumen, wherein the first segment axis of the first lumen is parallel to the first segment axis of the second lumen, and wherein the distal end of the second lumen is coupled to the second opening; and
a guide coupled to the plate.

2. The suture placement system of claim 1, wherein the second opening is located between the first opening and a point where the guide is coupled to the plate.

3. The suture placement system of claim 1, wherein the guide is removably coupled to the plate.

4. The suture placement system of claim 1, wherein the guide comprises a guide tube.

5. The suture placement system of claim 4, further comprising an attachment suture engaging the plate, passing through a distal end of the guide tube, and secured near a proximal end of the guide tube to keep the guide tube coupled to the plate.

6. The suture placement system of claim 5, further comprising a fastener securing the attachment suture near the proximal end of the guide tube.

7. The suture placement system of claim 1, wherein the plate comprises surface variations configured to make the plate visible on an echocardiogram.

8. The suture placement system of claim 1, further comprising a coating on the plate configured to make the plate visible on an echocardiogram.

9. The suture placement system of claim 1, further comprising a coating on the first and/or the second lumen configured to make the first and/or second lumen visible on an echocardiogram.

10. The suture placement system of claim 1, further comprising a coating on the guide configured to make the guide visible on an echocardiogram.

11. The suture placement system of claim 1, wherein at least a portion of the first segment of the first lumen and at least a portion of the first segment of the second lumen are bonded together.

12. The suture placement system of claim 1, wherein at least a portion of the first and second lumens are housed within a same suture tube.

13. The suture placement system of claim 1, further comprising a snare having a snare loop and a snare handle.

14. The suture placement system of claim 13, wherein the snare is at least partially located within the second lumen, such that at least a portion of the snare loop extends from the distal end of the second lumen, while at least a portion of the snare handle extends from the proximal end of the second lumen.

15. The suture placement system of claim 1, further comprising an implant suture having a first ferrule on a first end of the implant suture and a second ferrule on a second end of the implant suture.

16. The suture placement system of claim 15, wherein the implant suture is partially located within the first lumen, such that the first end of the implant suture with the first ferrule extends from the distal end of the first lumen, while the second end of the implant suture with the second ferrule extends from the proximal end of the first lumen.

17. The suture placement system of claim 16, wherein:
the implant suture comprises one or more markings to differentiate the first end of the implant suture from the second end of the implant suture.

18. The suture placement system of claim 1, further comprising a follower for coupling to a minimally invasive suturing device and configured for slideable engagement with the guide, wherein the follower defines a cross-sectional shape compatible for slideable engagement with the guide.

19. The suture placement system of claim 18, wherein the follower defines a cross-sectional shape compatible for slideable engagement which is selected from a group consisting of circular, oval, square, rectangular, triangular, notched, and keyed.

20. The suture placement system of claim 18, further comprising the minimally invasive suturing device, wherein the follower is coupled to a distal tip of the minimally invasive suturing device.

21. The suture placement system of claim 1, further comprising a suture lock coupled to the proximal end of the first lumen and a suture lock coupled to the proximal end of the second lumen.

22. The suture placement system of claim 1, wherein at least a portion of the first segment of the first lumen is in contact with at least a portion of the first segment of the second lumen.

23. The suture placement system of claim 1, wherein a first distance between the intermediate point and the proximal end of the first segment of the first lumen is equal to a second distance between the intermediate point and the proximal end of the first segment of the second lumen.

24. The suture placement system of claim 23, wherein the obtuse angle between the axis of the second segment of the first lumen and the first segment axis of the first lumen is equal to the obtuse angle between the axis of the second segment of the second lumen and the first segment axis of the second lumen.

* * * * *